United States Patent
Jensen

(10) Patent No.: US 7,983,851 B2
(45) Date of Patent: Jul. 19, 2011

(54) MEASURING DEVICE AND METHOD FOR DETERMINATION OF AT LEAST ONE CHEMICAL PROPERTY IN AN OIL AND A DATA STORING DEVICE OBTAINABLE BY SAID METHOD

(75) Inventor: Ole Jensen, Aalborg (DK)

(73) Assignee: Nanonord A/S, Aalborg (DK)

( * ) Notice: Subject to any disclaimer, the term of this patent is extended or adjusted under 35 U.S.C. 154(b) by 435 days.

(21) Appl. No.: 12/083,464

(22) PCT Filed: Oct. 13, 2006

(86) PCT No.: PCT/DK2006/050060
§ 371 (c)(1),
(2), (4) Date: Apr. 11, 2008

(87) PCT Pub. No.: WO2007/042051
PCT Pub. Date: Apr. 19, 2007

(65) Prior Publication Data
US 2009/0164139 A1    Jun. 25, 2009

(30) Foreign Application Priority Data

Oct. 13, 2005 (DK) .................................. 2005 01434

(51) Int. Cl.
*G01N 33/08* (2006.01)
(52) U.S. Cl. .................... 702/25; 250/339.09; 702/30
(58) Field of Classification Search .................. 702/25, 702/30, 47, 52, 91, 93, 104, 116; 73/28, 73/49, 61.44; 250/339.09
See application file for complete search history.

(56) References Cited

U.S. PATENT DOCUMENTS

| 3,181,058 | A | 4/1965 | Gulbrandsen |
| 4,215,567 | A | 8/1980 | Vlcek |
| 4,704,898 | A | 11/1987 | Thone |
| 5,132,225 | A | 7/1992 | Dickakian |
| 5,722,469 | A | 3/1998 | Tuminaro |
| 6,452,179 | B1 | 9/2002 | Coates et al. |
| 7,194,369 | B2 * | 3/2007 | Lundstedt et al. ............ 702/104 |

FOREIGN PATENT DOCUMENTS

| EP | 0 928 883 | 7/1999 |
| EP | 1 134 574 | 5/2006 |
| GB | 1 442 893 | 7/1976 |
| GB | 2 400 364 | 4/1999 |
| JP | 11-116000 | 10/2004 |
| WO | 2005/021419 | 3/2005 |

* cited by examiner

*Primary Examiner* — John H Le
(74) *Attorney, Agent, or Firm* — Buchanan Ingersoll & Rooney PC

(57) ABSTRACT

A measuring system for determination of at least one chemical property in an oil under transportation from a first container to a second container, where a pipe inlet is arranged to withdraw a sample part from the oil in flow and a sample handling arrangement is arranged for guiding a sample from the sample part into and out of at least one chemical property measuring instrument. The measuring system further includes a control computer unit connected to the sample handling arrangement and being programmed to performing a plurality of consecutive measuring cycles, each including i) guiding a sample from the sample part into the at least one chemical property measuring instrument, ii) performing a measurement of the at least one chemical property in the sample, and iii) withdrawing the sample from the at least one chemical property measuring instrument.

53 Claims, 3 Drawing Sheets

MEASURING DEVICE AND METHOD FOR DETERMINATION OF AT LEAST ONE CHEMICAL PROPERTY IN AN OIL AND A DATA STORING DEVICE OBTAINABLE BY SAID METHOD

TECHNICAL FIELD

The invention relates to a measuring system for determination of at least one chemical property in an oil under transportation from a first container to a second container. The invention also relates to a method of determination of at least one chemical property in an oil under transportation from a first container to a second container as well as a data storing device with data obtainable from such measurement.

BACKGROUND ART

Many systems and instruments for measuring selected properties of an oil have been described in the art. Measuring systems measuring physical properties of oils, such as viscosity are standard in the art and are used widely for determine the quality of an oil. In particular when transporting large amount of an oil from one container to another it is often desired to make sure that the transported oil has the desired quality.

WO 05021419 describe a vehicle misfuelling alert apparatus for use with a fuel pump having at least one fuel nozzle. The apparatus includes a transmitter for transmitting a data signal and positioned on the bodywork of a vehicle adjacent the fuel tank inlet of the vehicle. A receiver is positioned on the fuel nozzle adjacent the handle portion. The data signal contains a unique fuel code which represents the type of fuel required by the vehicle. The receiver has a predetermined set of stored data that represents the type of fuel dispensed by the fuel nozzle. When a motorist presents the fuel nozzle to the fuel tank inlet, the receiver will receive the data signal transmitted by the transmitter and alerts the motorist by means of an indicator if the data signal does not match the stored data (i.e. if the fuel dispensed by the fuel nozzle is not the type of fuel required by the vehicle).

This misfuelling alert apparatus does not measure any property of the fuel, but compare only an fuel type identification signal transmitted from the vehicle to the fuel dispenser to identify if this type of fuel is dispensed from this fuel dispenser. In practice such an alert apparatus is only useful is specific situations, such as situation where possibly variations within the type of fuel is not relevant or not existing A similar fuel dispensing system is disclosed in U.S. Pat. No. 5,722,469. This system additionally comprises a contamination detection device which during fuel loading measures the specific gravity of the fuel to thereby detect possibly contaminations.

U.S. Pat. No. 4,704,898 discloses an apparatus for measuring the viscosity of a liquid. The viscosity meter is determining the viscosity using an oscillating damping system and the viscosity is determined by way of a comparison of the energy absorbed with the energy absorbed in a liquid of known viscosity. The viscosity meter disclosed may e.g. be utilized in order to monitor the viscosity of a liquid which is required to be delivered to a customer with given quality features, e.g. bunker fuel for delivering to a ship. The viscosity meter may be arranged within the bunker pipe 58 for measuring the viscosity of the fuel flowing through the bunker pipe 58.

The above described prior art systems are often suitable when measuring on general homogenous oils, or where the composition of the oil is relatively well known, However, many types of oil are in practice a mixture of hydrocarbons of different sizes and a plurality of other constituents, such as inorganic components, and/or more or less dispersed particles. The viscosity may be very high to very low for the same oil batch to be transported from one container to another, and in general it has been found that the viscosity cannot stand alone for determinate the oil quality.

Many of these types of oils are very inhomogeneous, and the composition and quality thereof cannot be measured by simply withdrawing a sample and sending it to a text lab.

Within the art of bunker fuel, sample collection has become an important discipline, due to the difficulties in collecting representative samples from a bunker fuel under loading. The general accepted sampler systems are systems based on sampling small amounts during loading and pooling the sample for quality test. The most used samplers are drip samplers.

The object of the invention is to provide a measuring system which provide an effective and fast method of determining quality of an oil irrespectively of the inhomogeneity of the oil

DISCLOSURE OF INVENTION

According to the invention it has thus been found that a pooled sample does not provide a true picture of the quality of the oil. The inhomogeneous oil will gradually be used, e.g. by being transported to an engine, and in this gradually use the oil may still be as inhomogeneous at it is during transport from a first to a second container. It has thus been found that to obtain a true picture of the quality of an inhomogeneous oil, the degree of inhomogeneity is as important as the average level of the relevant constituents.

According to the invention a novel measuring system for determination of at least one chemical property in an oil under transportation from a first container to a second container has thus been provided. The measuring system of the invention is defined in the claims.

It should be emphasized that the term "comprises/comprising" when used in this specification is taken to specify the presence of stated features, integers, steps or components but does not preclude the presence or addition of one or more other stated features, integers, steps, components or groups thereof.

The measuring system of the invention has been found to be very reliable and fast. The time factor may in some embodiments be of high importance, as it will be clear from the following description of the system.

The measuring system of the invention comprises for determination of at least one chemical property in an oil under transportation from a first container to a second container, said system comprising a pipe inlet arranged to continuously or stepwise withdraw a sample part from the oil in flow under transportation from said first container to said second container, a pipe outlet for discharging at least some of the sample part, at least one chemical property measuring instrument for measuring a chemical property in a sample of said sample part, a sample handling arrangement for guiding a sample from said sample part into and out of said at least one chemical property measuring instrument, wherein said measuring system further comprises a control computer unit connected to said a sample handling arrangement and being programmed to performing a plurality of consecutive measuring cycles, each comprising i. guiding a sample from said sample part into said at least one chemical property measuring instrument,
ii. performing a measurement of said at least one chemical property in said sample, and
iii. withdrawing said sample from said at least one chemical property measuring instrument.

Physical properties are properties that relates to the fluid as such (contrary to components of the fluid only) and that can be observed without changing the identity of the substance. As examples of physical properties can be mentioned color, smell, refractive index, viscosity and density.

Chemical property are properties that is not within the definition of physical properties, and includes properties that relates to the chemical composition of the oil, such as the presence or the amount of one or more components in the oil, its chemical reactivity, its pH value and similar.

'Measuring a property' means obtaining data relating to said property from one measuring instrument. 'Determining a property' means obtaining data (directly or by calculation) relating to said property from data obtained from one measuring instrument and/or obtaining data calculated from data obtained from 2 or more measuring instruments.

According to the invention the system is capable of determining at least one chemical property in an oil under transportation from a first container to a second container.

In practice the oil may be of any hydrocarbon oil, e.g. oils ranging from crude oil to vegetable oil. Since the measuring is in particular beneficial to explore inhomogeneity in oils, it may preferably be used for determining properties in oils which are at least suspected for being inhomogeneous. The oil may thus preferably be selected from the group consisting of crude oil, bunker fuel lubricant, hydraulic oil, gasoline, such as diesel and petrol and vegetable oil, such as palm oil.

In a preferred embodiment the measuring system is adapted to use in the examination of bunker fuel. Bunker fuel is also known by other names, such as heavy oil, #6 oil, resid, Bunker C, blended fuel oil, furnace oil and other often locally used names. Bunker fuel is obtained from crude oil after the lighter fractions (gasoline, kerosene, diesel, etc.) are removed by distillation. The heaviest materials in crude petroleum are not distilled—the boiling points are too high to be conveniently recovered. These materials (asphaltenes, waxes, very large molecules, etc.) carry through refining and become residual oil (or bunker fuel). During various operations in the refinery (principally heating at high temperatures), rearrangement of molecules may take place forming even larger molecular materials that have still higher boiling point. These materials also become part of the bunker fuel. Finally, any contaminants in the crude will not be distilled from the crude and will also be in the bunker fuel. This includes any salts, sediment (oil-wetted solids), and the heavy organic molecules from various sources. The bunker fuel may be diluted e.g. by lead containing gasoline. Diluted bunker fuel is within the definition of bunker fuel as used herein.

Anything that doesn't distillate during refining carries into the bunker fuel. This includes not only water soluble metal salts sodium (Na), chlorides (Cl) (e.g. from seawater), potassium (K), calcium (Ca), sulphates (=SO4), and several others, but also the oil soluble metals vanadium (V), lead (Pb), nickel (Ni) and others as well as suspended solids. Vanadium and nickel may e.g. be present as porphyrins, which are very large molecules, and does not distillate during refining from crude oil. Oil wetted materials such as rust and metal particles may also be present.

The measuring system may preferably be used for examining oils in large quantities, such as oils in quantities of at least 50 litres, such as 100 litres, such as 1000 litres or more.

In practice it can be said that the larger the oil quantity, the more beneficial will the system be. Fore example it can be mentioned that the amount of marine lubricant transferred to a ship is relatively large. Quantities of 10,000 litres or more are not uncommon. The measuring system could thus be used to detect the marine lubricant on loading from a car tank, vessel, drums or similar onto the lubricating reservoir on a ship. Similar the system could be used under loading of bunker fuel, which is often loaded on to a ship in even larger quantities, such as 10,000-5,000,000 litres.

The measuring system is arranged to withdraw a sample part from the oil in flow under transportation from a first container to a second container.

The first and the second containers may in practice be any kind of containers e.g. tanks, vessels and drums as already mentioned above.

In one embodiment of the invention the first container is a supply reservoir, such as a tank, a vessels or a drum for supplying fresh oil to a unit, such as an airplane, a ship (e.g. a container ship or an oil tanker) or similar transportation unit. The second container may thus preferably be a fuel tank, a lubricant reservoir or similar on said transport unit.

In one embodiment the first and the second container is the same container, and the oil is withdrawn from this container through a pipe and returned to said container, preferably at a distance from the point of withdrawing. In this embodiment the first and the second container may e.g. be a lubricant reservoir e.g. on a ship. The lubricant may be examined e.g. as to the amount of water which has entered the lubricating system. As it is well known to a skilled person, seawater may enter a marine lubricating system e.g. via a stern-tube and that may lead to substantial risk of damage to the bearings and shaft, as well to undesired corrosion. Corrosion may lead to release of e.g. constituent metals of essential bearings within the lubricating system. Tracing the concentration of seawater as well as other corrosion prompting elements helps diagnosing the status/mechanical integrity of the lubricated parts.

By using the system of the invention the quality of the marine lubricant may be examined at desired intervals. In this way the time for changing lubricant may be extended. In this embodiment the measuring system may e.g. be arranged to withdraw sample part prom a pipe leading to or from a circulation pump for circulating lubricant.

The system comprises a pipe inlet arranged to continuously or stepwise withdraw a sample part from the oil in flow under transportation from said first container to said second container. The term 'sample part' is herein used to designate the amount of oil withdrawn from the oil flow whereas the term 'sample' means a sample that is subjected to a measurement. In one embodiment the whole sample part may be subjected to a measurement, however this will mainly be measurement of a physical property, such as viscosity.

In one embodiment the pipe inlet is arranged to withdraw a sample part from the oil in flow under transportation from the first container to the second container in consecutive steps. The consecutive stem may have a frequency which differs from or is equal to the frequency of the measuring cycles. The frequency of the consecutive steps is measured as the number of times a step is initiated (i.e. when a vent is opening through which the sample part is withdrawn) within a given time. The frequency of the measuring cycles is measured as the number of times a measuring cycle is initiated within a given time.

The sample part may preferably be withdrawn from a connecting pipe connecting the first container to the second container. The connecting pipe designate the one or more pipes through which the oil is flowing. Thus in one embodiment the sample part is withdrawn from a fuel pump pipe or a lubricating supply pipe. In one embodiment the sample part is withdrawn from an inlet section to the second container, such as an inlet pipe to a fuel tank or a lubricant reservoir, e.g. a bunker inlet pipe The arrangement for withdrawing the sample part may include one or more valves, control systems, control computers and similar equipments, which will be well known to the skilled person.

The sample part may preferably be a relatively small fraction of the total amount of oil, e.g. up to about 5%. In one example the amount of oil withdrawn from the connecting pipe is at least 0.1 l/hour, such as between 1 and 100 l/hour. In practice the type of measuring instruments and the number of measuring cycles may set a minimum requirement of the amount of oil in the sample part. In other word, the sample part should be sufficient large for the desired measurement to be performed.

In one embodiment the pipe inlet is arranged to stepwise withdraw a sample part from the oil flow under transportation. The amount of oil withdrawn in the individual steps of withdrawing oil may in practice be any fraction of the total sample part, such as at least 0.05 l, such as between 0.1 and 25 l per step. When the oil is bunker fuel, the amount of oil withdrawn in each step may in practice be between above 0.2 litres, such as between 0.5 and 5 litres.

The system may be arranged to withdraw sample part stepwise with regular or irregular steps, which in practice may have any length. The length of a withdrawing step is measured from initiation (i.e. when a vent is opening through which the sample part is withdrawn) of one step, to initiation of the subsequent step.

The time for each stepwise withdrawning sample part and the size of said sample part may preferably be recorded e.g. on a data storing device.

The term 'measuring cycles' designate a repeating handling comprising
 i) guiding a sample from said sample part into said at least one chemical property measuring instrument,
 ii) performing a measurement of said at least one chemical property in said sample, and
 iii) withdrawing said sample from said at least one chemical property measuring instrument.

A measuring cycle may comprise additional actions/handling, such as adjusting temperature, performing separation steps and e.t.c. The plurality of measuring cycles may be arranged to be performed with varying or with an equidistant cycle time. The cycle time is measured from initiation of one measuring cycles to initiating of a subsequent measuring cycles. The control computer unit may preferably be programmed to control the frequency and of the measuring cycles and the cycle time.

The control computer unit may in practice be any kind of computerized control unit. It may be one physical unit or it may be separated in two or more communicating computer units. In the following the computer is described a one unit, but it should be interpreted to also encompass several communicating computer units.

The sample handling arrangement is controlled by said control computer unit, and may in principle be arranged with any pipe sections, valves, chambers and similar for handling the sample. Such arrangements can by ordinary means be provided by a skilled person, based on the teaching provided herein.

In one preferred embodiment the control computer unit is programmed to perform a plurality of consecutive measuring cycles, with an equidistant cycle time for each cycle.

The cycle time may in one embodiment be up to one hour. Preferably the cycle time should be sufficient short for a representative number of measurements to be performed. Thus it is preferred that the control computer unit is programmed to perform the cycle time so that at least 10, measurements, such as at least 20 measurements, such as at least 100 measurements is performed under the transport of the oil from a first to a second container. In preferred embodiments the cycle time is between 0.5 to 30 minutes, such as between 1 and 10 minutes.

In one embodiment wherein the pipe inlet is arranged to stepwise, in consecutive steps, withdrawing a sample part from the oil flow under transportation, and these consecutive steps has a step time, and the control computer unit is programmed to perform at least one cycle series of plurality of consecutive measuring cycles, the control computer unit may be programmed to performed said at least one cycle series with a cycle time which is less than said step time of withdrawing sample part, preferably so that at least two measurement can be performed on samples from one on samples from one sample part withdrawn from the oil flow under transportation in one or preferably each step.

Said two or more measurements on samples from one sample part withdrawn in same sample part withdrawing step, may be used as separate measurements and/or the average value, and variation on the measurements may be calculated there from e.g. by a computing unit, which may e.g. be in data communication with the control computer unit.

In general it is preferred that two or more type measurements are performed. These measurements may be performed in the same cycle series comprising a plurality of consecutive measuring cycles, or it may be performed in perform in two or more cycle series of plurality of consecutive measuring cycles.

In one embodiment the said control computer unit is programmed to make the system perform two or more cycle series of plurality of consecutive measuring cycles, each cycle series comprising
 i. guiding a sample from said sample part into at least one measuring instrument selected from a chemical property measuring instrument, a physical property measuring instrument and both chemical property and physical property measuring instrument,
 ii. performing a measurement in said sample, and
 iii. withdrawing said sample from said at least one measuring instrument.

The term 'chemical property measuring instrument' designate an instrument which is arranged to perform at least one chemical measurement. The term 'physical property measuring instrument' designate an instrument which is arranged to perform at least one physical measurement. The term 'measuring instrument' designates both chemical property measuring instruments and physical property measuring instruments. Some measuring instruments may be both a chemical property measuring instruments and a physical property measuring instrument.

Any measuring instruments may in principle be employed in the system of the invention, provided that the measurement can be performed relatively fast and preferably automatically, without human intervention until the measuring result is obtained. Of useful measuring instruments, may e.g. the following be mentioned:
 Viscosity meters, such as 'Oval Gear Flowmeters' from JLC International.
 Temperature meters, such as model MBT3560, MBT5560 or similar from Danfoss as well as model 7MF1564-XXX from Siemens.

Density measuring instruments, such a model "Viscomaster", "Viscomaster Dynamic" from Mobrey, Emerson Processing Control as well as model FC 300 and MASS 2100 Mass Flow Meter from Siemens.

X-ray fluorescence measuring instruments, such as model SINDIE in-line analyzer from XOS inc. and model 682P-EC from Spectro Analytical Instruments.

Water content measuring instrument, such as model EASZ-1 from EESIFLO

After measurement, some of the sample may be discharged to a container, but it is in general preferred that the used samples is returned to the main oil stream (the oil in flow under transportation), e.g. via the sample part.

When the pipe inlet is arranged to continuously a sample part from the main oil stream, is generally preferred that the pipe outlet for discharging at least some of the sample part is arranged to discharge said oil e.g. to the main oil stream in a continuous manner preferably with same velocity as the continuous withdrawal of the sample part.

When the pipe inlet is arranged to stepwise withdraw a sample part from the main stream, which in practice is preferred because it provides a more accurate picture of any inhomogeneities in the oil, it is preferred that said or the major part of said sample part is discharged prior to taking in a new sample part in a subsequent sample part withdrawing step.

In one embodiment the system is arranged to discharge at least some of the sample part back to the oil in flow under transportation.

The one or more chemical property may in principle be selected from any chemical property. In practice the optimal chemical properties to determine is dependant on which type of oil is under examination. Most often is it desired to determine the presence and/or the amount of at least one component within the oil, preferably the amount of one or more inorganic components.

In one embodiment the chemical property being selected from the group consisting of
concentration of water
concentration of sulphur (S)
concentration of aluminum (Al)
concentration of silicon (Si)
concentration of vanadium (V)
concentration of sodium (Na)
concentration of calcium (Ca)
concentration of chlorine (Cl)
concentration of zinc (Zn),
concentration of phosphorous (P)
concentration of non-burnable ash,
oil stability,
and combinations thereof The above chemical property or properties are in particular relevant when the oil is a bunker fuel as explained above.

In one embodiment wherein the oil is bunker fuel the chemical property determined comprises one or more of the following, e.g. in addition to one or more of the above mentioned:
Concentration of iron (Fe).
Concentration of nickel (Ni).
Concentration of hydrogen sulphide.

Simultaneously with the chemical properties one or more physical properties may preferably be measured. The measuring system may therefore in one embodiment comprise at least one physical property measuring instrument for measuring a physical property of the oil, said physical property preferably being selected from the group consisting of
density—arranged to be measured in a sample of said sample part,
viscosity—arranged to be measured in a sample of said sample part,
velocity—arranged to determine the oil flow velocity in said flow of oil under transportation, and
combinations thereof.

In one embodiment wherein the measuring system is adapted for examining a lubricant the at least one physical/chemical property measuring instrument being arranged to measure at least one of the properties:
Total acid number (TAN),
Concentration of KOH and/or alkalinity
Concentration of insolubilities
Concentration of Water
Presence and or concentration of one or more of the components selected from the group consisting of Aluminum (Al), Chromium (Cr), Copper (Cu), Iron (Fe), Lead (Pb), Nickel (Ni), Silicon (Si), Sodium (Na), Tin (Sn), Vanadium (V), Antimony (Sb),
Flash point and
kinematic viscosity.

In one embodiment the measuring system comprises at least two, such as at least three, such as at least four measuring instruments selected from chemical property measuring instruments, physical property measuring instruments and both chemical property and physical property measuring instruments.

It is generally preferred the performed measurements are recorded on a data storing device, simultaneously it is preferred that the point of time of the measuring cycles is recorded for identifying the time of the various measurements. The data storing device may be any type of memory unit, preferably electronic memory unit. The measuring system may comprise two or more data storing devices for recording the various date. In the following the term 'data storing device' is referred to in singular, but it should be understood that the system of the invention may comprise several data storing devices e.g. locally arranged data storing devices as well as centrally arranged data storing devices. The term 'data storing device' is used to designate any kind of memory units locally or centrally. In a preferred embodiment a single data storing device comprises at least one data series obtained from a plurality of consecutive measurement cycles of at least one cycle series.

In one embodiment the measuring system of the invention comprises a recording unit for recording the point of times of the measuring cycles of the one or more measuring instruments in relation to the flow of the oil under transportation, preferably the measuring system comprises a physical measuring instrument for determine the oil flow velocity in said flow of oil under transportation for thereby determine the amount of oil transported at the point of time for each of the measuring cycles of the one or more chemical measuring instruments and/or physical measuring instruments.

The point of time for a measuring cycle may preferably be defined to be the time for initiating withdrawing a sample from the sample part or if measured directly in the sample part, the time for performing the measurement.

The data storing device may preferably be a part of, or is in data transmitting connection with the control computer unit.

Data transmitting connection means in this context that data can be transmitted wireless or through a physical connection.

In one embodiment the measuring system may further comprise a computing device, which preferably is a part of, or is in data transmitting connection to the control computer unit.

The computing device may be programmed to perform calculations based on the obtained measurement to thereby obtain the desired chemical and physical determinations.

Further information relating to the determination of properties in petroleum products, including bunker fuel may be found in ISO standard 8217:2005(E).

In one embodiment the measuring system comprises at least one measuring instrument for measuring at least one chemical property and/or physical property relating to the burning value of the oil selected from the group consisting of the concentration of water, the concentration of sulphur (S) and the concentration of non-burnable ash, the viscosity and the density. The computing device may preferably be programmed to calculate and record an approximately burning value based on the at least one chemical property and/or physical property relating to the burning value of the oil. The at least one chemical property and/or physical property preferably comprise(s) the concentration of water.

The term 'burning value' includes the standardized determinations of net specific energy and Calculated Carbon Aromaticity Index (CCAI), as well as other determinations relating to the burning value of the oil.

In one embodiment the measuring system comprises at least one measuring instrument for measuring at least one chemical property and/or physical property relating to abrasive content of the oil selected from the group consisting of the concentration of silicon (Si), the concentration of aluminum (Al), the concentration of calcium (Ca) and the viscosity. The computing device is preferably programmed to calculate and record an approximately abrasive content based on this at least one chemical property and/or physical property relating to the abrasive content of the oil. Preferably the at least one chemical property and/or physical property preferably comprise(s) the concentrations of Al and Si.

The term 'abrasive content' relates to the content of inorganic components with abrasive effect on the system in which the oil is adapted to be used.

In one embodiment the measuring system comprises at least one measuring instrument for measuring at least one chemical property and/or physical property relating to the concentration of corrosive metallic species of the oil selected from the group consisting of the concentration of silicon (Si), the concentration of aluminum (Al), the concentration of vanadium (V), the concentration of sodium (Na), the concentration of zinc (Zn), and the concentration of iron (Fe). The computing device being programmed to calculate and record an approximately corrosive metallic species value based on said at least one chemical property and/or physical property relating to the concentration of corrosive metallic species of the oil. It is preferred that said at least one chemical property and/or physical property preferably comprises the concentration of V and Na. Na in particular has a tendency to form a corrosive salt layer onto the turbo supercharger in a ship engine.

In one embodiment the measuring system comprises at least one measuring instrument for measuring at least one chemical property and/or physical property relating to concentration of used lubricating oils (ULOs) of the oil selected from the group consisting of the concentration of zinc (Zn), the concentration of phosphorous (P), the concentration of iron (Fe), the concentration of lead (Pb) and the concentration of calcium (Ca). The computing device may preferably be programmed to calculate and record an approximately concentration of ULOs based on said at least one chemical property and/or physical property relating to the concentration of ULOs of the oil. The at least one chemical property and/or physical property preferably comprises the concentration of zinc (Zn), the concentration of phosphorous (P) and the concentration of zinc (Zn), the concentration of phosphorous (P).

The definition of ULOs can be found in ISO standard 8217:2005(E).

In one embodiment the computing device is programmed to calculate the variance of the data relating to at least one property of the oil, comprising the measured and/or said calculated properties of the oil. By use of this calculated variance a measure for the inhomogeneity of the oil can be obtained.

The measuring system may preferably comprises at least one data storing device for storing said measured and/or said calculated data relating to one or more properties of the oil, said storing device preferably being a part of, or is in data transmitting connection with the control computer unit.

In one embodiment the measuring system further comprises a standard data storing device storing standard data for one or more of the measured and/or said calculated properties of the oil. The standard data storing device being a part of, or is in data transmitting connection with the data storing device.

Standard data may e.g. be obtained from previous measurement or it may be an indication of upper/lower level of properties in the oil. By comparing the determined properties with standard data a good picture of the quality of the oil under examination can be obtained.

In one embodiment the storing device being connected to a computer for comparing the measured and/or said calculated data relating to one or more properties of the oil with the standard data for one or more of the measured and/or said calculated properties of the oil.

In one embodiment the measuring system comprises a density measuring instrument for measuring density at two or more different temperatures. The density measuring instrument may preferably be linked to a computing device programmed to determinate the density of the oil at a specific temperature, preferably said specific temperature being 15° C.

Standards for performing such calculations are well known to the skilled person.

In one embodiment the measuring system comprises an X-ray fluorescence measuring instrument for measuring chemical components in the oil. The X-ray fluorescence measuring instrument may in principle be arranged to measure presence and/or concentration of any components which can be detected with such an X-ray fluorescence measuring instrument. In a preferred embodiment the X-ray fluorescence measuring instrument is programmed to measure the content of one or more of the components S, V, Si, Al, Cl and Ca in the oil.

In one embodiment the X-ray fluorescence measuring instrument comprising a sample chamber and is arranged for measuring on an oil sample in the sample chamber. The X-ray fluorescence measuring instrument comprising an X-ray emitter, which may be of any kind, such as a radioactive source (calibrated or uncalibrated solid source) or a low-power radioactive source. The X-ray fluorescence measuring instrument further comprises a florescence detector for detecting energy/wavelength transmitted by electron transitions in atoms in the oil.

The florescence detector may e.g. be wavelength dispersive or energy dispersive.

In one embodiment the X-ray fluorescence measuring instrument further comprises a cooling device arranged to cool a sample in the sample chamber. By cooling the sample the vapor pressure will be decreased and it will be possibly to arrange the detector very close to the sample with no disturbing elements, such as a window as well as volatile hydrocarbons between the sample and the detector. The measurement performed may therefore be much more accurate than by using the known X-ray fluorescence measuring instrument. The sample may e.g. be cooled to a temperature below 0° C., such as between −5 and −40° C., e.g. about −30° C.

In a preferred embodiment the florescence detector of the X-ray fluorescence measuring instrument is therefore arranged immediately adjacent to the sample free of solid material in between said sample surface and said florescence detector.

In one embodiment the sample chamber is filled with helium above the sample to avoid attenuation of fluorescent radiation by air constituents like e.g. Argon, Nitrogen and Oxygen. In another embodiment vacuum is applied above the sample.

The florescence detector may be any useful detector, such as a Charge Coupled Device (CDD).

In one embodiment the measuring system comprises a water content measuring instrument for measuring the concentration of water. The water measuring instrument is preferably arranged to performing batch wise measurements.

The water content measuring instrument may preferably comprise an evaporating chamber for evaporating water from an oil sample, a condensation chamber for condensing the evaporated water, a capacitive meter for measuring the relative dielectric constant $\in_r$ of the condensed water, and a unit for measuring the amount of condensate. In one embodiment the water content measuring instrument is linked to a computing device programmed to determinate the water content in the sample based on data comprising the data measured by the water content measuring instrument.

Since the relative dielectric constant $\in_r$ of water is much higher than that of hydrocarbons a very accurate determination of the water content can be obtained using such water content measuring instrument based on measuring the relative dielectric constant $\in_r$.

The evaporating chamber may preferably be a vacuum evaporating chamber and comprises vacuum pump. By using a vacuum evaporating chamber a fast evaporation can be obtained. In a preferred embodiment an ultrasonic device is arranged for applying ultrasonic energy to a sample in the vacuum evaporating chamber. Ultrasonic energy has shown to increase the amount of water which possibly can be evaporated from the oil, and thereby an even more accurate water determination can be obtained.

The evaporated water may e.g. be condensed in the condensation chamber by cooling the electrodes. Thereby the condensed water will simultaneously be applied onto the electrodes of the capacitive meter The capacitive meter may in principle comprise electrodes of any shape and size. In a preferred embodiment the capacitive meter comprises a pair of pipe shaped electrodes inserted into each other. Thereby the electrode pair has a relative large surface compared to its volume.

The relative dielectric constant $\in_r$ may preferably be measured at an AC frequency of above 40 KHz, such as between 45 and 60 KHz, such as about 50 KHz.

In one embodiment the capacitive meter has a circular electrode chamber to increase the surface area and avoid irregularities that exists in e.g. a square construction. The amount of condensate may e.g. be measured as its volume/weight in the circular electrode chamber In one embodiment of the measuring system control, the computer unit is directly connected or is wireless connected to one or more computing device programmed to perform calculation based on data for one or more of the measured properties of the oil, one or more storing device arranged to store data for one or more of said measured and/or said calculated properties of the oil, and one or more standard data storing device storing standard data for one or more of said measured and/or said calculated properties of the oil. The measuring system preferably further comprises a screen for presenting the data from the one or more storing devices.

In one embodiment of the measuring system it preferably further comprise an evidence sample collecting unit, comprising an evidence sample outflow, and an evidence sample valve connected to said evidence sample outflow. The evidence sample valve may be connected to the control computer unit, and the control computer unit may be programmed to open the evidence sample valve to discharge an evidence sample through the evidence sample outflow when one or more of the measured and/or the calculated properties of the oil exceed a standard data for the one or more properties.

The evidence sample collecting unit may preferably comprise a holder for holding a sample collecting container for collecting said discharged evidence sample.

By collecting such sample from a sample part with properties below a desired set value, evidence of low quality, unacceptable inhomogeneity and similar may be obtained. Such evidence samples is in particular desired when the oil is delivered to a customer e.g. when examining a bunker fuel under loading to a ship.

The terms as used for the description of the system, have the same meaning throughout the application.

The invention also relates to a data storing device comprising at least one series of data obtainable by the system as described above and where the stored data relates to one or more properties of an oil, wherein each individual data of said at least one series of data is linked to a volume related data, wherein said volume related data being selected from the group consisting of, an amount of oil transported through a pipe, a velocity of oil transported through a pipe, a time value and combinations thereof.

Such storing device may be used for benchmarking for future measurements performed using the system of the invention. The data storing device may e.g. comprise data for two or more examinations of oil under transport from a first to a second container. In one embodiment the data storing device comprises data from examination of a plurality of properties of bunker fuel under loading from a delivering container to a ship tank.

The invention further relates to a method of determine of at least one chemical property in an oil under transportation from a first container to a second container. The method of the invention comprises continuously or stepwise withdrawing a sample part from the oil in flow under transportation from said first container to said second container, continuously or stepwise discharging at least a part of said sample part performing a plurality of consecutive measuring cycles, each cycle comprising withdrawing at least one sample from said sample part and measuring at least one chemical property in said sample.

The method may preferably be performed using a measuring system as described above.

The oil examined by the method and the properties measured may likewise be as above.

In one embodiment of the method of the invention the sample part is collected from a connecting pipe connecting the first container to the second container. The connecting pipe, the point of withdrawing the sample part, the amount of sample part withdrawn, the mode of withdrawing the sample part and the containers may e.g. be as described above.

In the method of the invention the cycle time for the plurality of consecutive measuring cycles may be as disclosed above, and the method may likewise comprise two or more cycle series.

According to the method of the invention it is often desired to determining at least two, such as at least three, such as at least four physical/chemical properties in the sample part or in samples withdrawn from said sample parts.

The data obtained by the measurement may as described above be used for various calculation and determinations, such as determination of water content, determination of burning value, determination of abrasive content, determination of concentration of corrosive metallic species, determination of content of ULOs, calculation of the variance of the data relating to at least one property of the oil, calculation of the quality of the oil and similar.

The data obtained may further be compared to standard data as described above.

In one preferred embodiment of the method, the method comprises comparing data relating to at least one property in a sample withdrawn from a sample part or in a sample part with a standard data of this at least one property, and withdrawing an evidence sample from said sample part if said data relating to at least one property exceed said standard data.

The invention will be explained more fully below in connection with an example and with reference to the drawings. It should be stressed that the invention is not limited to the example and embodiments shown on the drawings, but may be embodied in other ways within the subject-matter defined in the claims.

Figure 1:
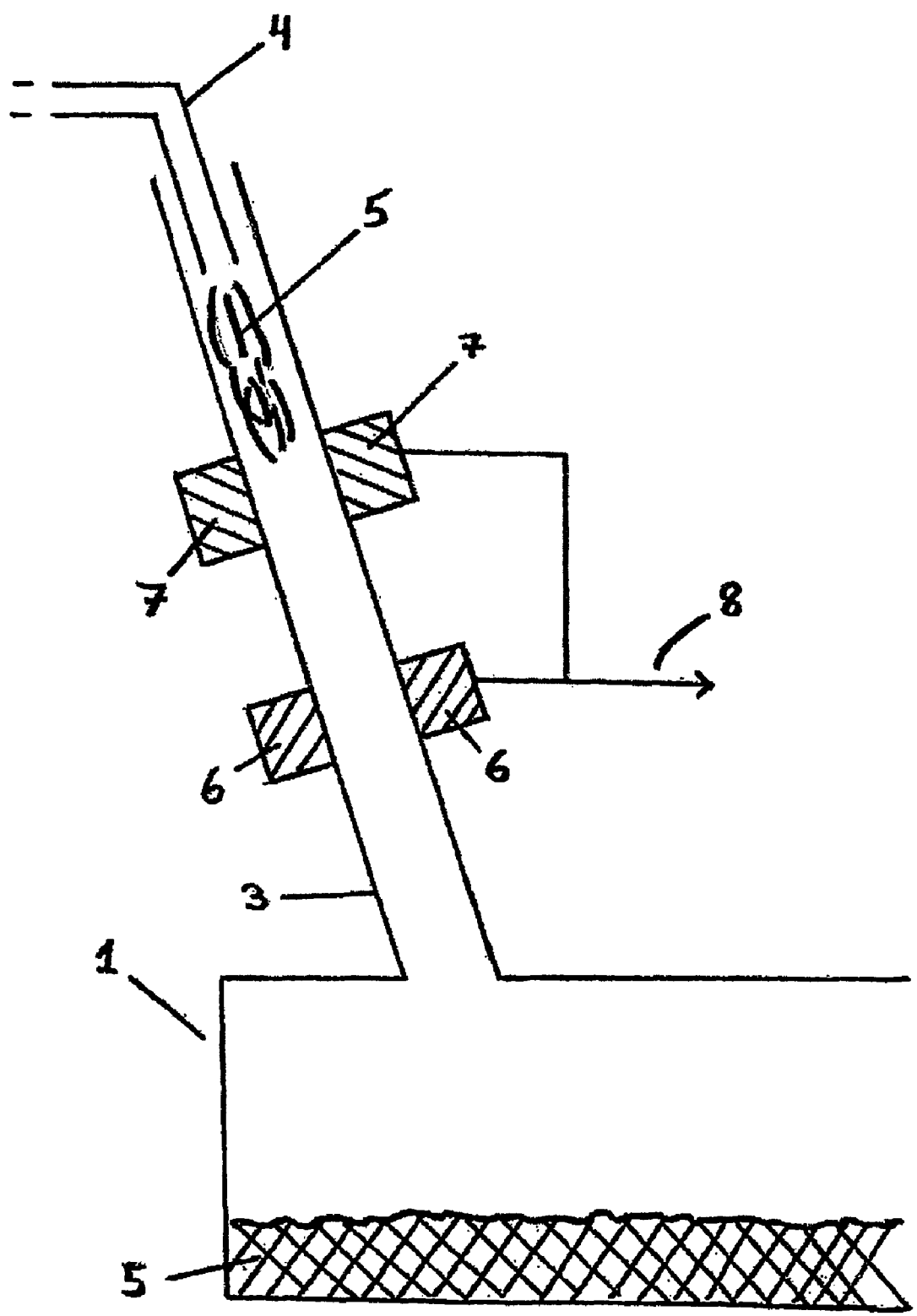
FIG. 1 shows a side sectional cut of a part of a connection pipe leading to a fuel tank, to which connection pipe a system according to the invention is connected.
Figure 2:
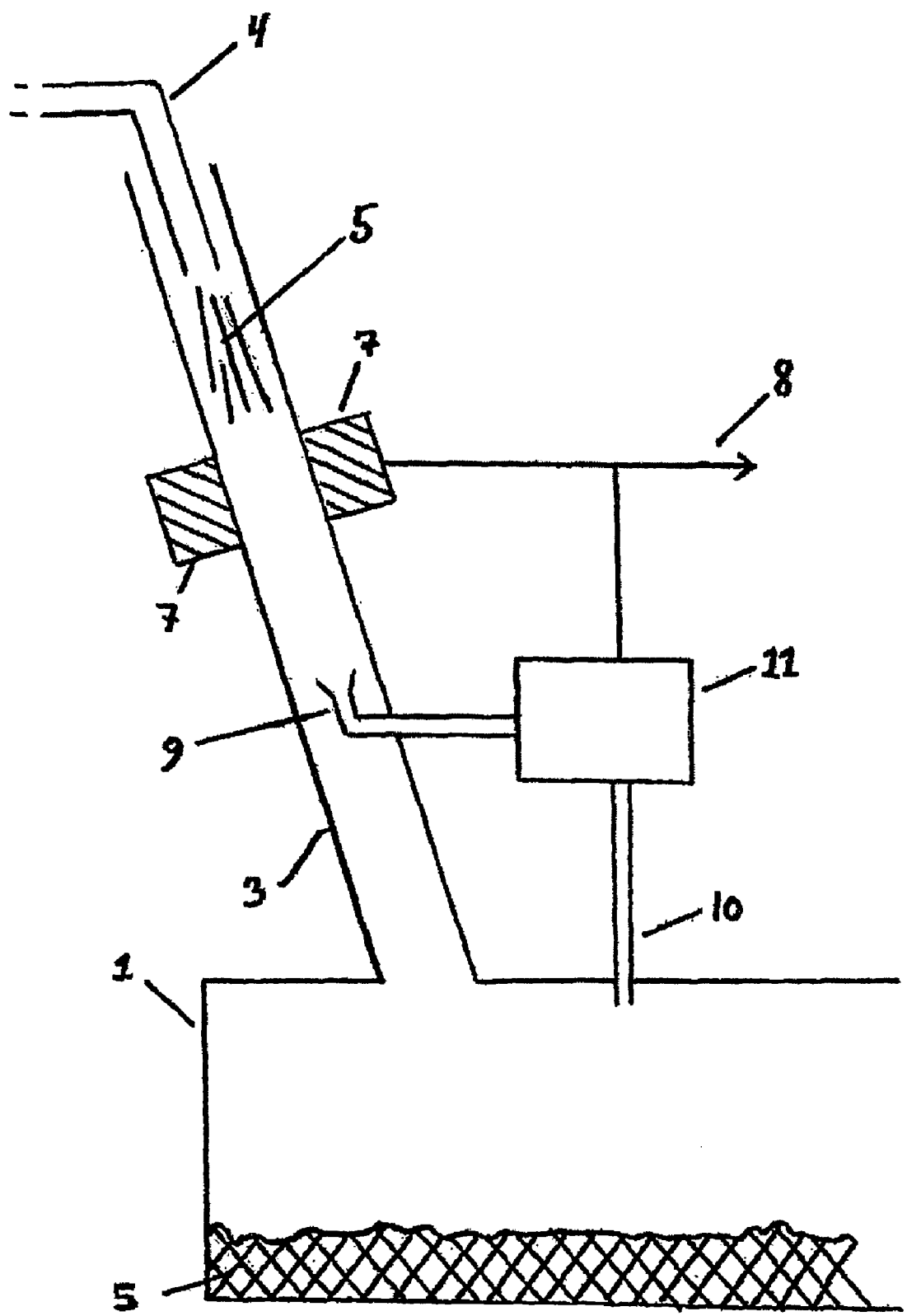
FIG. 2 shows a side sectional cut of a part of a connection pipe leading to a fuel tank, to which connection pipe another system according to the invention is connected.

The part of the connection pipe shown in FIG. 1 comprises an inlet section 3 to a fuel tank 1, and a fuelling pipe 4 through which fuel 5 is feed into the fuel tank 1. The fuel 5 is guided from a not shown container, e.g. a fuel pump container.

A measuring system 6, according to the invention is placed immediately adjacent to the inlet section 3 to the fuel tank 1. The measuring system comprises not shown measuring instruments as described above. The measuring system 6 may e.g. comprise an instrument for screening with light, e.g. laser light, where the interaction between the fuel 5 and the laser light can be detected and used for determining the fuel type and quality. Other possibly realizations of the measuring system 6 comprises measuring the interaction between the fuel 5 and ionization radiation, such as gamma radiation or x-ray radiation.

Some of the measuring may be performed directly on the flowing fuel 5. For a large number of chemical measuring types it is however preferred to perform the measurement on samples withdrawn from the main fuel stream.

The measuring system 6 comprises a control computer unit 8, which is programmed to control the function of the measuring system 6 as described above. The control computer unit 8 may further be connected to a closing unit 7 e.g. a valve, which can close the inlet section for loading of fuel 5.

The computer unit may be programmed to compare one or more detected property of the fuel with a set date (e.g. standard data for upper/lover threshold limits). The control computer unit 8 may give a signal and/or simply activates the closing unit 7 if one or more determined property/properties of the fuel exceed the set value for this/these property/properties.

The measuring system and its connection to the connection pipe is a variation of what is shown in FIG. 1. In this embodiment the inlet section 3 to the fuel tank 1 is connected to measuring system 11 according to the invention by a sample part withdrawing pipe 9, capable of withdrawing a sample part from the main fuel stream. Sample part(s) withdrawn from the main fuel stream is transported to the measuring system 11 where it is examined. After examination the fuel is transported via pipe section 10 to the fuel tank.

The fuel tank may beneficially be a fuel tank on a ship, and the fuel may e.g. be bunker fuel. Also for environmental reasons more and more requirements to the quality of bunker fuel are demanded. In particular more and more requirements to the contents of various inorganic matters as described above e.g. sulphur are demanded. In international ships industry the demand as to the content of sulphur in bunker fuel may be set according to ASTM standard D 4294.

The ASTM standard D 4294 may e.g. be used as standard data for comparing determined property (properties) in the measuring system 11. These standard data may e.g. be stored in the memory of a not shown control computer unit 8. Sulphur content may e.g. be measured using an X-ray fluorescence measuring instrument.

A desired analysis time may e.g. be 2-4 minutes.

The not shown control computer unit 8, is programmed to control the function of the measuring system 11 as described above. The control computer unit 8 may further be connected to a closing unit 7 e.g. a valve, which can close the inlet section for loading of fuel 5. The closing unit 7 may alternatively being activated manually e.g. upon an alarm signal from the control computer unit 8.

The data obtained may beneficially be stored as described above.

Figure 3:
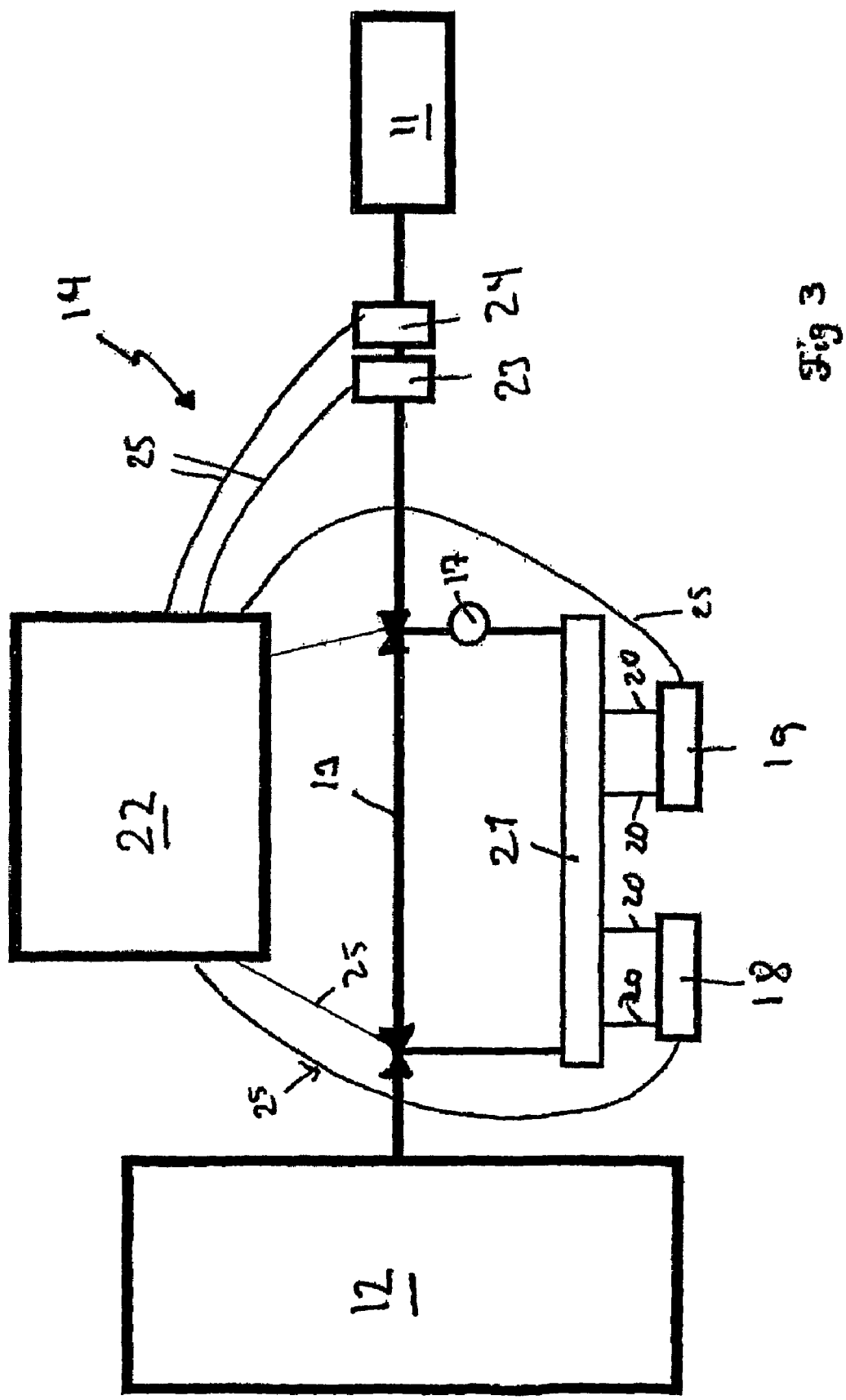
FIG. 3 is a schematic drawing of a measuring system according to the invention

FIG. 3 is a drawing of a measuring system (lab-on-a-ship) according to the invention. The drawing is purely schematic. The drawing show an engine 11 of a ship, a fuel tank 12 and a consumption pipe 13 connecting the fuel tank 12 to the engine 11 for supplying bunker fuel to the engine 11. Other not shown fittings, such as valves, pumps and similar may be arranged between the tank 12 and the engine 11, such as it is well known to the skilled person. A measuring system 14 according to the invention is connected to the consumption pipe 13 for determining of a number of properties of the bunker fuel.

The measuring system 14 comprises a pipe inlet 15 arranged to continuously or stepwise withdraw a sample part from the bunker fuel in flow under transportation from the fuel tank 12 to the engine 11 and a pipe outlet 16 for discharging at least some of the sample part back to the main bunker fuel stream in the consumption pipe 13. The pipe outlet 16 may e.g. comprise a pump and/or a valve 17. Additional pumps/valves may be arranged for controlling the system. The skilled person will be able to arrange this using his common general knowledge.

The measuring system 14 further comprises a sample part chamber 21 for the withdrawn sample part(s) and two measuring instruments 18, 19 connected to the sample part chamber 21 and from where samples can be withdrawn and discharged to via the pipes 20. The measuring instruments 18, 19 are in this example a water content measuring instrument and an x-ray fluorescence (XRF) measuring instrument.

The measuring system 14 further comprises additional measuring instruments 23, 24, for determining viscosity, density and temperature.

The measuring system 14 additionally comprises a control computer unit 22, which is connected to all the above described units for controlling the function of the system. On the drawing the connections between the control computer unit 22 and the other units of the measuring system 14 is indicated with wires 25. It should be understood that the connections could as well be wireless, such as it is well known in the art.

EXAMPLE

The Lab-on-a-ship system shown in FIG. 3 was tested onboard a ship (J. Lauritzen) Oct. 6, 2006 in Antwerp, Belgium.

The test consisted of acquisition of oil analysis data from the consumption pipe (i.e. fuel ready for usage in the ship engine) and real-time monitoring of the supplied bunker fuel.

The following parameters were determined: Density [kg/m3], viscosity [cSt], gas content [V/V, %], sulphur content [m/m, %], and vanadium content [m/m, %].

The density and viscosity were measured continuously at the inlet temperature of the oil by a combination of a Coriolis flow meter and a differential pressure gauge. Corresponding values of these parameters at the ISO specified referral temperatures were subsequently calculated using linear regression.

The main cycle time for the water content measuring and the XFR measuring was 5 min. The amount of sample used in respectively the water content measuring instrument and an X-ray fluorescence (XRF) measuring instrument was about 380 ml and about 1 ml.

The XRF unit facilitated measurements of the sulphur and vanadium content of the oil by exposing a 1 ml oil sample to X-rays from an encapsulated Fe-55 source and detecting the fluorescence peaks from the elements in the oil.

All data were updated real-time on a web server of oil quality from the control room of the ship. The web server was connected to the control computer unit 22.

The data measured in a test run was: 2.47% Sulphur versus Lloyds (reference) measurement of 2.49%, whereas the density was measured in the system to 982.5 kg/m3, versus Lloyds (reference) measurement was 985 kg/m3.

The above figures are schematic and simplified for clarity, and they just show details which are essential to the understanding of the invention, while other details are left out. Throughout, the same reference numerals are used for identical or corresponding parts.

What is claimed is:

1. A measuring system for determination of at least one chemical property in an oil under transportation from a first container to a second container, said system comprising
    a pipe inlet arranged to or stepwise in consecutive steps, withdraw a sample part from the oil in flow under transportation from said first container to said second container, said consecutive steps have a step time,
    a pipe outlet for discharging at least some of the sample part,
    at least two measuring instruments each for measuring a property in a sample of said sample part, at least one of said measuring instruments being a chemical property measuring instrument for measuring a chemical property,
    a sample handling arrangement for guiding a sample from said sample part into and out of each of said at least two measuring instruments,
    wherein said measuring system further comprises a control computer unit connected to said sample handling arrangement and programmed to perform a plurality of consecutive measuring cycles, each comprising
        i. guiding a sample from said sample part into each of said at least two measuring instruments,
        ii. performing a measurement of said respective properties by said respective measuring instruments in said respective samples, and
        iii. withdrawing said respective samples from said at least two measuring instruments
    said control computer unit being programmed to perform said at least one cycle series with a cycle time which is less than said step time.

2. The measuring system as claimed in claim 1 wherein said oil comprises a bunker fuel and said second container comprises a fuel tank.

3. The measuring system as claimed in claim 1 wherein said oil comprises an oil selected from the group consisting of lubricant, hydraulic oil, gasoline and vegetable oil.

4. The measuring system as claimed in claim 1 wherein said control computer unit is programmed to perform said plurality of consecutive measuring cycles, with an equidistant cycle time for each cycle.

5. The measuring system as claimed in claim 1 wherein said control computer unit is programmed to perform two or more cycle series of plurality of consecutive measuring cycles each cycle series comprising
    i. guiding a sample from said sample part into each of at least two measuring instruments selected from chemical property measuring instruments, physical property measuring instruments and both chemical property and physical property measuring instruments,
    ii. performing measurements in said samples, and
    iii. withdrawing said samples from said at least one measuring instruments.

6. The measuring system as claimed in claim 5 wherein said pipe inlet is arranged to stepwise, in consecutive steps, withdraw a sample part from the oil flow under transportation, said control computer unit is programmed to perform said at least one cycle series with a cycle time so that at least two measurements of at least one chemical property measuring instrument can be performed on samples from one sample part withdrawn from the oil flow under transportation in one each step.

7. The measuring system according to claim 6, wherein at least two measurement can be performed on samples from one sample part withdrawn from the oil flow under transportation in one each step.

8. The measuring system as claimed in claim 1, wherein said pipe outlet for discharging at least some of the sample part is arranged to discharge at least some of the sample part back to the oil in flow under transportation.

9. The measuring system as claimed in claim 1, wherein said at least one chemical property is selected from the group consisting of
    concentration of water
    concentration of sulphur (S)
    concentration of aluminum (Al)
    concentration of silicon (Si)
    concentration of vanadium (V)
    concentration of sodium (Na)
    concentration of calcium (Ca)
    concentration of chlorine (Cl)

concentration of zinc (Zn),
concentration of phosphorous (P)
concentration of non-burnable ash,
oil stability,
and combinations thereof.

10. The measuring system as claimed in claim 1, wherein the measuring system further comprises at least one physical property measuring instrument for measuring a physical property of the oil, said physical property being selected from the group consisting of
   density arranged to be measured in a sample of said sample part,
   viscosity arranged to be measured in a sample of said sample part,
   velocity arranged to determine the oil flow velocity in said flow of oil under transportation, and
   combinations thereof.

11. The measuring system as claimed in claim 1, wherein the measuring system comprises at least two measuring instruments selected from chemical property measuring instruments, physical property measuring instruments and both chemical property and physical property measuring instruments.

12. The measuring system as claimed in claim 1 wherein the measuring system comprises a data storing device for recording the point of time for a measuring cycle of the one or more measuring instruments in relation to the flow of the oil under transportation.

13. The measuring system as claimed in claim 12 wherein the data storing device is a part of, or is in data transmitting connection to the control computer unit.

14. The measuring system as claimed in claim 1, wherein the measuring system further comprises a computing device, said computing device being a part of, or being in data transmitting connection to the control computer unit.

15. The measuring system as claimed in claim 14 wherein said measuring system comprises at least one measuring instrument for measuring at least one chemical property and/or physical property relating to the burning value of the oil selected from the group consisting of
   the concentration of water,
   the concentration of sulphur (S)
   the concentration of non-burnable ash,
   the viscosity and
   the density,
said computing device being programmed to calculate and record an approximately burning value based on said at least one chemical property and/or physical property relating to the burning value of the oil.

16. The measuring system as claimed in claim 14 wherein said measuring system comprises at least one measuring instrument for measuring at least one chemical property and/or physical property relating to abrasive content of the oil selected from the group consisting of
   the concentration of silicon (Si),
   the concentration of aluminum (Al),
   the concentration of calcium (Ca) and
   the viscosity,
said computing device being programmed to calculate and record an approximately abrasive content based on said at least one chemical property and/or physical property relating to the abrasive content of the oil.

17. The measuring system as claimed in claim 14 wherein said measuring system comprises at least one measuring instrument for measuring at least one chemical property and/ or physical property relating to the concentration of corrosive metallic species of the oil selected from the group consisting of
   the concentration of silicon (Si),
   the concentration of aluminum (Al),
   the concentration of vanadium (V),
   the concentration of sodium (Na),
   the concentration of zinc (Zn), and
   the concentration of iron (Fe),
said computing device being programmed to calculate and record an approximately corrosive metallic species value based on said at least one chemical property and/or physical property relating to the concentration of corrosive metallic species of the oil.

18. A measuring Bunker fuel system as claimed in claim 14 wherein said measuring system comprises at least one measuring instrument for measuring at least one chemical property and/or physical property relating to concentration of used lubricating oils (ULOs) of the oil selected from the group consisting of
   the concentration of zinc (Zn),
   the concentration of phosphorous (P),
   the concentration of iron (Fe),
   the concentration of lead (Pb) and
   the concentration of calcium (Ca),
said computing device being programmed to calculate and record an approximately concentration of ULOs based on said at least one chemical property and/or physical property relating to the concentration of ULOs of the oil.

19. The measuring system as claimed in claim 14, wherein, said computing device is programmed to calculate the variance of the data relating to at least one property of the oil, comprising said measured and/or said calculated properties of the oil.

20. The measuring system as claimed in claim 1, wherein, said system further comprises at least one data storing device for storing said measured and/or said calculated data relating to one or more properties of the oil.

21. The measuring system as claimed in claim 1, wherein, said system further comprises a standard data storing device storing standard data for one or more of the measured and/or said calculated properties of the oil, said standard data storing device being a part of, or being in data transmitting connection with the data storing device.

22. The measuring system as claimed in claim 21 wherein said data storing device is connected to a computer for comparing said measured and/or said calculated data relating to one or more properties of the oil with said standard data for one or more of the measured and/or said calculated properties of the oil.

23. The measuring system as claimed in claim 1, wherein the measuring system comprises a density measuring instrument for measuring density at two or more different temperatures, said density measuring instrument being linked to a computing device programmed to determinate the density of the oil at a specific temperature.

24. The measuring system as claimed in claim 1, wherein the measuring system comprises an X-ray fluorescence measuring instrument for measuring chemical components in the oil.

25. The measuring system as claimed in claim 24 wherein the X-ray fluorescence measuring instrument comprises a sample chamber and is arranged for measuring on an oil sample in the sample chamber, the X-ray fluorescence measuring instrument comprising an X-ray emitter, and a florescence detector for detecting energy/wavelength transmitted by electron transmission in atoms in the oil.

26. The measuring system as claimed in claim 24, wherein the X-ray fluorescence measuring instrument further comprises a cooling device arranged to cool a sample in the sample chamber.

27. The measuring system according to claim 26, wherein said florescence detector is arranged immediately adjacent to the sample free of solid material in between said sample surface and said florescence detector.

28. The measuring system as claimed in claim 24, wherein said florescence detector is a Charge Coupled Device (CDD).

29. The measuring system as claimed in claim 1, wherein the measuring system comprises a water content measuring instrument for measuring the concentration of water, said measuring instrument performing batch wise measurements.

30. The measuring system as claimed in claim 29 wherein said water content measuring instrument comprises an evaporating chamber for evaporating water from an oil sample, an condensation chamber for condensing the evaporated water, a capacitive meter for measuring the relative dielectric constant $\in_r$ of the condensed water, and a unit for measuring the amount of condensate.

31. The measuring system as claimed in claim 30 wherein the evaporating chamber is a vacuum evaporating chamber and comprises a vacuum pump, and an ultrasonic device arranged for applying ultrasonic energy to a sample in said vacuum evaporating chamber.

32. The measuring system according to claim 31, wherein said capacitive meter comprises a pair of pipe shaped electrodes.

33. The measuring system as claimed in claim 30, wherein the unit for measuring the amount of condensate is a volume meter or a weight meter.

34. The measuring system as claimed in claim 1, wherein the control computer unit is directly connected or is wireless connected to one or more computing device programmed to perform calculation based on data for one or more of the measured properties of the oil, one or more storing device arranged to store data for one or more of said measured and/or said calculated properties of the oil, and one or more standard data storing device storing standard data for one or more of said measured and/or said calculated properties of the oil.

35. The measuring system as claimed in claim 34 wherein said measuring system further comprises an evidence sample collecting unit, comprising an evidence sample outflow, and an evidence sample valve connected to said evidence sample outflow, wherein said evidence sample valve is connected to said control computer unit, and said control computer unit is programmed to open said evidence sample valve to discharge an evidence sample through said evidence sample outflow when one or more of said measured and/or said calculated properties of the oil exceed a standard data for said one or more properties.

36. A data storing device comprising at least one series of data obtained by the system of claim 1 and comprising said respective properties obtainable by said respective measuring instruments in said respective samples for each sample part, wherein each individual data of said at least one series of data is linked to a volume related data, wherein said volume related data is selected from the group consisting of, an amount of oil transported through a pipe, a velocity of oil transported through a pipe, a time value and combinations thereof.

37. A method of determine of at least one chemical property in an oil under transportation from a first container to a second container, said method comprising
stepwise in consecutive steps, withdrawing a sample part from the oil in flow under transportation from said first container to said second container, said consecutive steps have a step time,
continuously or stepwise discharging at least a part of said sample part,
performing a plurality of consecutive measuring cycles, each cycle comprising withdrawing at least two samples from said sample part and measuring at least one property in each sample comprising at least one chemical property,
each measuring cycle having a cycle time which is less than said step time.

38. The method according to claim 37, wherein said method is performed using a measuring system for determination of at least one chemical property in an oil under transportation from a first container to a second container, said system comprising
a pipe inlet arranged to continuously or stepwise withdraw a sample part from the oil in flow under transportation from said first container to said second container,
a pipe outlet for discharging at least some of the sample part,
at least one chemical property measuring instrument for measuring a chemical property in a sample of said sample part,
a sample handling arrangement for guiding a sample from said sample part into and out of said at least one chemical property measuring instrument,
wherein said measuring system further comprises a control computer unit connected to said sample handling arrangement and programmed to perform a plurality of consecutive measuring cycles, each comprising
i. guiding a sample from said sample part into said at least one chemical property measuring instrument,
ii. performing a measurement of said at least one chemical property in said sample, and
iii. withdrawing said sample from said at least one chemical property measuring instrument.

39. The method according to claim 37 wherein said oil comprises a bunker fuel.

40. The method according to claim 37 wherein said oil being an oil selected from the group consisting of lubricant, hydraulic oil, gasoline, and vegetable oil.

41. The method according to claim 37, wherein said sample part is collected from a connecting pipe connecting the said first container to said second container, said sample part being collected from a part of the connecting pipe constituting the inlet to a fuel tank of a ship.

42. The method according to claim 37, wherein said sample part of oil withdrawn from the connecting pipe is at least 0.1 l/hour.

43. The method according to claim 37, wherein said plurality of consecutive measuring cycles is performed with an equidistant cycle time for each cycle.

44. The method according to claim 37, wherein at least some of the sample part is discharged back to the oil in flow under transportation.

45. The method according to claim 37, wherein said at least one chemical property is selected from the group consisting of
concentration of water
concentration of sulphur (S)
concentration of aluminum (Al)
concentration of silicon (Si)
concentration of vanadium (V)
concentration of sodium (Na)

concentration of calcium (Ca)
concentration of chlorine (Cl)
concentration of zinc (Zn),
concentration of phosphorous (P)
concentration of non-burnable ash,
oil stability,
and combinations thereof.

46. The method according to claim 37, wherein said method further comprises measuring at least one physical property in the flow of oil under transportation, in the sample part or in a sample withdrawn from the sample part, said physical property being selected from the group consisting of
  density arranged to be measured in a sample of said sample part,
  viscosity arranged to be measured in a sample of said sample part,
  velocity arranged to determine the oil flow velocity in said flow of oil under transportation, and
  combinations thereof.

47. The method according to claim 37, wherein the method further comprises recording the times of the measuring cycles in relation to the flow of the oil under transportation, said method comprising measuring the oil flow velocity in said flow of oil under transportation for thereby determining the amount of oil transported at the point of time for each of the measuring cycles.

48. The method according to claim 37, wherein said method comprises determining at least one chemical property and/or physical property relating to the burning value of the oil selected from the group consisting of
  the concentration of water,
  the concentration of sulphur (S),
  the concentration of non-burnable ash,
  the viscosity and
  the density,
wherein said method further comprises calculating and recording an approximately burning value based on said at least one chemical property and/or physical property relating to the burning value of the oil.

49. The method according to claim 37, wherein said method comprises determining at least one chemical property and/or physical property relating to abrasive content of the oil selected from the group consisting of
  the concentration of silicon (Si),
  the concentration of aluminum (Al),
  the concentration of calcium (Ca) and
  the viscosity,
wherein said method further comprising calculating and recording an approximately abrasive content based on said at least one chemical property and/or physical property relating to the abrasive content of the oil.

50. The method according to claim 37, wherein said method comprises determining at least one chemical property and/or physical property relating to concentration of corrosive metallic species of the oil selected from the group consisting of
  the concentration of silicon (Si),
  the concentration of aluminum (Al),
  the concentration of vanadium (V),
  the concentration of sodium (Na),
  the concentration of zinc (Zn), and
  the concentration of iron (Fe),
wherein said method further comprises calculating and recording the corrosive metallic species value of the oil based on said at least one chemical property and/or physical property relating to concentration of corrosive metallic species.

51. The method according to claim 37, wherein said method comprises determining at least one chemical property and/or physical property relating to concentration of used lubricating oils (ULOs) of the oil selected from the group consisting of
  the concentration of zinc (Zn),
  the concentration of phosphorous (P)
  the concentration of iron (Fe),
  the concentration of lead (Pb) and
  the concentration of calcium (Ca),
wherein said method further comprises calculating and recording an approximately concentration of ULOs based on said at least one chemical property and/or physical property relating to the concentration of ULOs of the oil.

52. The method according to claim 37, wherein said method comprises calculating the variance of the data relating to at least one property of the oil.

53. The method according to claim 37, comprising comparing a data relating to at least one property in a sample withdrawn from a sample part or in a sample part with a standard data of said at least one property, and withdrawing an evidence sample from said sample part if said data relating to at least one property exceed said standard data.

* * * * *